United States Patent [19]

Schumann

[11] Patent Number: Plant 7,392

[45] Date of Patent: Dec. 11, 1990

[54] GERANIUM PLANT NAMED FISBAL

[75] Inventor: Ingeborg Schumann, Hoehr-Grenzhausen, Fed. Rep. of Germany

[73] Assignee: Florfis AG, Binningen, Switzerland

[21] Appl. No.: 426,174

[22] Filed: Oct. 25, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of Geranium plant named Fisbal, particularly characterized by the combined features of white semi-double flowers, medium to dark green leaves with good chlorophyll stability, resulting in better transporting ability, less susceptibility to rain damage, fast rooting, compact habit, excellent branching, and free standing flowers.

1 Drawing Sheet

The present invention comprises a new and distinct cultivar of Geranium, botanically known as *Pelargonium zonale,* and hereinafter referred to by the cultivar name Fisbal.

Fisbal is a product of a planned breeding program which has the objective of creating new geranium cultivars with white semi-double flowers, medium to dark green leaves, better transportation ability, fast rooting, better temperature tolerance, and moderate nutrient or feeding requirements.

Fisbal was originated from a hybridization made by the inventor in a controlled breeding program in Hillscheid, Federal Republic of Germany, in 1982.

The female parent was Perlpenei, a cultivar having white semi-double flowers with light green foliage (quite often with chlorosis). The male parent of Fisbal was the cultivar Leif Danzig, having white single flowers, good zonation, very tall growing habit and bad chlorophyll quality.

Fisbal was discovered and selected as one flowering plant within the progeny of the stated cross by Ingeborg Schumann in May 1983 in a controlled environment in Hillscheid, Federal Republic of Germany.

The first act of asexual reproduction of Fisbal was accomplished when vegetative cuttings were taken from the initial selection in February 1984 in a controlled environment in Hillscheid, Federal Republic of Germany by, or under the supervision of, Ingeborg Schumann.

Horticultural examination of selected units initiated in Spring 1984 and continuing thereafter has demonstrated that the combination of characteristics as herein disclosed for Fisbal are firmly fixed and are retained through successive generations of asexual reproduction.

Fisbal has not been observed under all possible environmental conditions. The phenotype may vary significantly with variations in environment such as temperature, light intensity and daylength.

The following observations, measurements and comparisons describe plants grown in Hillscheid, Federal Republic of Germany, under greenhouse conditions which approximate those generally used in commercial practice.

The following traits have been repeatedly observed and are determined to be basic characteristics of Fisbal, which, in combination, distinguish this Geranium as a new and distinct cultivar:

1. White semi-double flowers.
2. Medium to dark green leaves.
3. Fast rooting.
4. Good temperature tolerance.
5. Good branching.
6. Flowers free standing above the leaves.

Of the many commercial cultivars known to the present invention, the most similar in comparison to Fisbal is the female parent, Perlpenei. In comparison to Perlpenei, Fisbal has a much darker leaf color (137A-B vs. 137C-D), longer flower stem (15.9 cm vs. 10.5 cm), better resistance to rain, better transportation ability, faster rooting, better tolerance to salt, better branching, and reduced feeding or fertilization needs.

The accompanying color photographic drawing shows typical flower and foliage characteristics of Fisbal, with the colors being as true as possible with illustrations of this type.

In the following description color references are made to The Royal Horticultural Society Colour Chart (R.H.S.). The color values were determined between 11:00 a.m. and 12:00 noon indoors on May 6, 1987 under 30,000 Lux light intensity at Hillscheid, Federal Republic of Germany.

Classification:

*Botanical.*—*Pelargonium zonale* l'Hert. cv Fisbal.

*Commercial.*—Zonal geranium.

INFLORESCENCE

A. Umbel:

*Average diameter.*—Indoor, 10.3 cm; outdoor 9.3 cm.

*Average depth.*—Indoor, 5.4 cm; outdoor, 5.1 cm.

*Peduncle length.*—Indoor, 15.9 cm; outdoor, 13.4. cm.

*Pedical length.*—Indoor, 2.8 cm; outdoor, 3.0 cm.

B. Corolla:

*Average diameter.*—Indoor, 4.3 cm; outdoor, 4.1 cm.

*Form.*—Semi-double.

*Color (general tonality from a distance of three meters).*—White.

*Color (upper and lower surfaces).*—R.H.S. 155D; wilting flowers turn slightly pink.

C. Bud:

*Shape.*—Round.

*Color.*—Light green.

*Sepals and pedicel.*—light green without anthocyan.

D. Reproductive organs:

*Androecium.*—5 fertile stamens.

*Gynoecium.*—5 lobed stigma.

E. Spring flowering response period: In Hillscheid, Federal Republic of Germany in 1988, 50% of plants with at least 1 flower opened 11 weeks after planting of unrooted cuttings in week 6.

F. Outdoor flower production: The flower count in 1988 in Hillscheid, Federal Republic of Germany indicated between 50 and 60 flowers per plant for June through October observation period.

G. Durability: Medium.

PLANT

A. Foliage:

*Form.*—Kidney shaped.

*Margin.*—Bicrenate.

*Color.*—Medium to dark green.

*Zonation.*—Weak, darker green.

*Tolerance to botrytis.*—Good.

B. General appearance and form:

*Internode length.*—Short.

*Branching pattern.*—4.7 branches per plant after 13 weeks of growing time from unrooted cuttings.

*Height.*—24 cm.

I claim:

1. A new and distinct cultivar of Geranium plant named Fisbal, as illustrated and described.

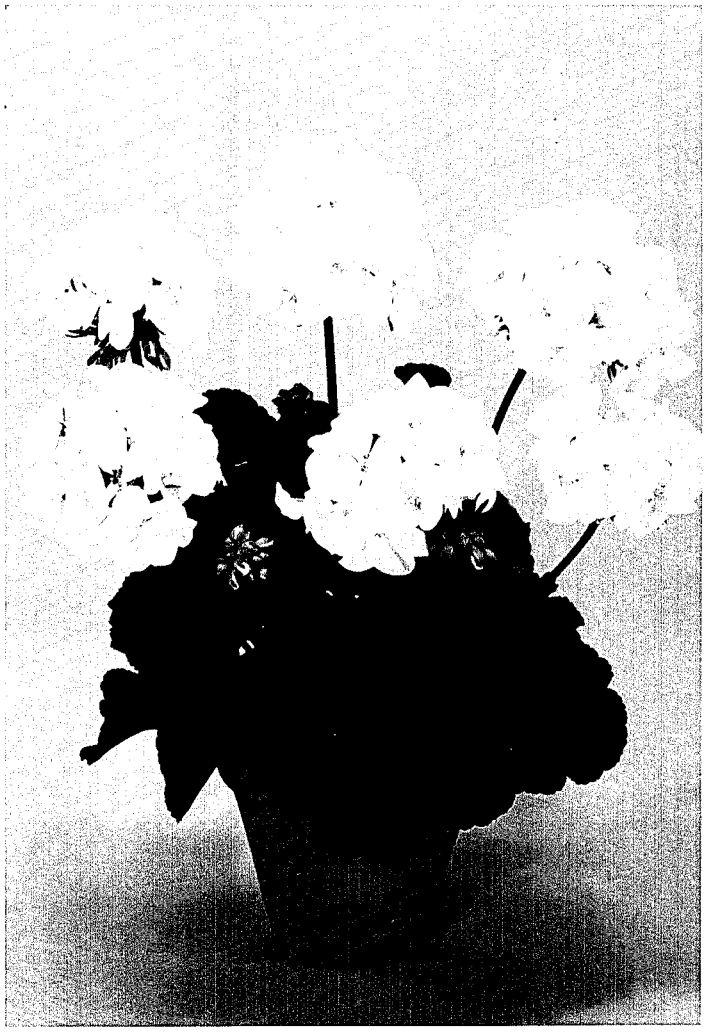

* * * * *